(12) United States Patent
Kumar et al.

(10) Patent No.: US 6,270,831 B2
(45) Date of Patent: Aug. 7, 2001

(54) METHOD AND APPARATUS FOR PROVIDING A CONDUCTIVE, AMORPHOUS NON-STICK COATING

(75) Inventors: B. Ajit Kumar; Pratap Khanwilkar; Don B. Olsen, all of Salt Lake City, UT (US)

(73) Assignees: MedQuest Products, Inc.; University of Utah Research Foundation, both of Salt Lake City, UT (US)

( * ) Notice: Subject to any disclaimer, the term of this patent is extended or adjusted under 35 U.S.C. 154(b) by 0 days.

(21) Appl. No.: 09/071,371

(22) Filed: Apr. 30, 1998

(51) Int. Cl.[7] ....................................... A61L 13/00
(52) U.S. Cl. ................ 427/2.24; 427/2.1; 427/2.3; 427/126.1; 427/127; 427/128; 427/162; 427/165; 427/255.4; 427/399; 438/1
(58) Field of Search ................ 204/192.1; 427/126.1, 427/127, 128, 2.1, 2.24, 2.3, 162, 165, 255.4, 399; 438/1

(56) References Cited

U.S. PATENT DOCUMENTS

| | | |
|---|---|---|
| 4,556,607 * | 12/1985 | Sastri . |
| 5,120,596 | 6/1992 | Yamada . |
| 5,152,774 | 10/1992 | Schroeder . |
| 5,324,289 | 6/1994 | Eggers . |
| 5,380,320 | 1/1995 | Morris . |
| 5,549,604 | 8/1996 | Sutcu et al. . |
| 5,630,275 * | 5/1997 | Wexler . |
| 5,658,282 | 8/1997 | Daw et al. . |
| 5,697,926 | 12/1997 | Weaver . |
| 5,720,775 | 2/1998 | Larnard . |
| 5,774,326 * | 6/1998 | McConnelee et al. . |

FOREIGN PATENT DOCUMENTS 0 479 482 A1    4/1992   (EP) .

* cited by examiner

*Primary Examiner*—Bernard Pianalto
(74) *Attorney, Agent, or Firm*—Holland & Hart LLP

(57) ABSTRACT

A conductive, non-stick coating is provided using a ceramic material which is conductive, flexible and provides a surface which exhibits the property of lubricity. A room or near room temperature manufacturing process produces a coating of titanium nitride on a substrate, where the coating is amorphous if the substrate is a solid material including plastics, composites, metals, magnets, and ceramics, enabling the substrate to bend without damaging the coating. The coating can also be applied as a conformal coating on a variety of substrate shapes, depending upon the application. The coating is bio-compatible and can be applied to a variety of medical devices.

39 Claims, 3 Drawing Sheets

METHOD AND APPARATUS FOR PROVIDING A CONDUCTIVE, AMORPHOUS NON-STICK COATING

BACKGROUND OF THE INVENTION

1. Field of the Invention

This invention pertains to a method for providing a conductive, non-stick coating at or near room-temperature to many materials which can benefit therefrom. More specifically, the present invention pertains to a method and apparatus for applying the conductive, non-stick coating to different materials, as well as presenting various embodiments which can take advantage of the coating's properties including bio-compatibility, flexibility, radio-opacity, diffusion resistance, wear and corrosion resistance, hardness, ability to be hydrophobic or hydrophilic, adherence to multiple materials, sterilizability, and chemical inertness and stability.

2. State of the Art

The present invention was originally developed as a result to improve electrosurgical instruments used in cauterization and other medical procedures, as well as to provide a bio-compatible coating for long-term implantable blood pumps. For example, prior U.S. patents have been issued for various electrosurgical blades which apply a non-stick coating to a cutting edge thereof. These blades typically suffered from small openings in the non-stick coating which were sometimes intentionally allowed to form in order to ensure electrical conductivity along the cutting edge. Exposing the metallic surface of the blade disadvantageously resulted in charred tissue sticking to these areas. The result was that the blade quickly became non-conductive and consequently unusable.

In an attempt to improve the blade, Blanch was granted U.S. Pat. No. 4,785,807 (the '807 patent) for teaching an electrosurgical blade which has a cutting edge of the blade which is abraded or etched, and a coat of a non-stick fluorinated hydrocarbon material which is applied over the etched cutting edge. A coating of non-stick material covers the surface area of the cutting blade and is intended to eliminate or reduce the clinging of charred tissue to the blade. By eliminating the small openings in the non-stick coating of previous blades, the blade better inhibited the build up of charred tissue. However, one drawback in the principle of the '807 patent is that the non-stick coating is not particularly durable, and will wear off after repeated usage. This is true partly because the non-stick and non-conductive coating has the properties of an insulator and had to be kept thin in order to enable the radio-frequency energy to pass through the non-stick coating to the tissue to cut and/or cauterize.

Another drawback of the blade described in the '807 patent is that the non-stick coating is not flexible. This inability to bend the electrosurgical blade seriously limits the options of the surgeon in the surgical procedures in which the blade can be used. Furthermore, bending the electrosurgical blade causes the non-stick coating to fracture. The electrosurgical blade then begins to rapidly build up charred tissue because of exposed etched metal of the blade, and any advantages of the non-stick coating are lost.

The non-stick coating of the '807 patent is also specifically described as Teflon (™). The nature of Teflon (™) is such that it requires a high current to be used in cutting and cauterization. This is because electrical current must pass through the Teflon (™) to the tissue. However, this constant passage of current eventually breaks down the Teflon (™), leaving small holes or other imperfections in the Teflon (™) coating. Charred tissue then begins to adhere to the exposed metal beneath the Teflon (™) coating. Furthermore, electrical current will no longer be uniform across the blade because the current will tend to concentrate at locations where the metal is exposed.

Another problem in the state of the art electrosurgical blades which utilize Teflon (™) is that when heated, Teflon disadvantageously breaks down and evolves fluorine as a gas. This gas is hazardous to the patient and the surgical team.

The information above introduces some of the problems of other non-stick coatings. However, the problems are associated specifically with the issues which are involved when using the non-stick coating for electrosurgical instruments. There are actually numerous other embodiments of the present invention which are able to take advantage of the characteristics of the conductive, non-stick coating which was originally developed to solve problems relating to electrosurgical instruments, blood pumps, and other medical devices.

There are also other problems with state of the art medical devices which are made from materials which do not react well or ideally with body tissue. For example, stents can cause infection and thrombosis, and have lubricity problems. Stents also clot up after some period of time, and the body can form scar tissue around the stent. A bio-compatible coating having greater lubricity and which is flexible enough to expand with the stent when deployed. Stents also tend to stick to the catheter that is used to insert them.

Catheters also have lubricity problems. They can be difficult to insert, especially when they are long. They are also hard to extract because they can become stuck. Present coatings that are used on catheters usually do not remain on the catheter, and either have the property of bio-compatibility or lubricity, but not both. Nonbio-compatible coatings are usually inflexible and cannot be applied to flexing plastics such as catheters. Friction during insertion also removes biological and polymeric coatings, and they also wash off when exposed to flowing fluids, such as blood. The tip of the catheter and the insertions site also tend to be the site of blood clots. These problems are exacerbated for balloon catheters in which the balloon sticks to the tissue or tears, releasing potentially dangerous gases into the body.

It is also of interest to recognize that most catheters use a radio-opaque metal band to denote the catheter position using X-ray imaging. This band disadvantageously causes crimping of the catheter. The metal band is also known to slip along the length of the catheter, thereby causing false readings of the catheter position in the body. The metal band providing radio-opacity is also typically large. This can result in insertion and extraction problems for the catheter. The metal band can also irritate and damage the inner surface of the vessel through which the catheter is inserted.

Guide wires used to install catheters also have problems of lubricity because they provide a frictional surface which resists entry into and passage through tissue.

The installation of a shunt is a painful process because of the friction of the tissue. Furthermore, state of the art shunts are also limited in their useful lifespan because they tend to have bio-compatibility problems.

Needles such as those used in dialysis and for diabetics which are of large diameter can also cause substantial pain during insertion and cause significant tissue damage.

Silicone-based medical devices such as inhaler seals, laryngechtomy prostheses, and nasal tampons have several major problems. The solid silicone is sticky and rubbery, and thus these devices are hard to insert and withdraw due to lubricity problems. Some of these devices are also subject to infection and thrombosis.

Trocars are also medical devices which would benefit from a bio-compatible coating having a high degree of lubricity. Trocars are used to introduce larger-sized implants and/or surgical tools, especially for minimally invasive surgery. Like needles, they have friction problems and can cause damage at the site of insertion.

Soft tissue implants such as breast, penile, and testicular implants, as well as devices such as pulsatile mechanical blood pumps suffer from diffusion problems. In the case of breast implants, huge liability has been incurred from silicone leaking out and causing potential systemic harm to the body. In the case of blood pumps, their pumping gases and fluids leak out, with potentially harmful side effects, as well as inconvenience caused by additional implanted hardware to replace lost fluids and added cost and inconvenience to the patient who has to make repeated trips to the hospital. Also, body fluids leak in, causing the corrosion of components which eventually cause device failure. These corrosion problems are also faced by implantable electrodes, leads, and sensors such as those of pacemakers and defibrillators. Drug containers also have problems of corrosion and chemical reactions, especially with the newer and more potent drugs, as well as of diffusion of drugs through the container, including the rubber stoppers used as the caps of some drug containers.

It is also mentioned that syringe components such as plungers often get stuck or caught while pulling in fluid. Often, excessive force is used while expelling fluids. These situations all combine to reduce patient safety because of increased risk of injury.

These are also similar problems to contraceptive and OB/Gyn devices which have problems with infection, thrombosis, tissue growth and friction causing irritation and subsequent trauma to surrounding tissue. Likewise, grafts and cuffs such as vascular grafts and varicose vein cuffs have problems with infection and thrombosis. Electrodes, especially those used for esophageal pacing, fetal monitoring, spinal epidural, and for ablation have problems of assuring electrical conductivity to the skin.

A different problem is raised by electro medical devices which suffer from failures caused by inadequate electromagnetic interference (EMI) shielding. Often, this failure relates to the use of plastic and other non-metallic parts in the electrical assembly that cannot be easily shielded.

Non-medical devices have other problems as well that could be solved by a coating as described above. For example, magnets have hydrogen embrittlement and subsequent degradation problems. These problems are acute in the new high-strength rare-earth magnets (e.g. Neodymium Iron Boron). This happens because hydrogen diffuses into the material and causes failure. Hydrogen embrittlement is also a problem in the aircraft industry with titanium and other structural materials.

Another problem that could be solved with a coating as described above is the sticking inside of a mold. The molded part sometimes sticks to the mold, destroying the part or the mold. Molds are presently made primarily of metal or ceramics, which makes then very expensive to make.

Disk drives might also benefit from the present invention. Specifically, EMI problems and friction problems could be eliminated with a coating like the present invention.

Another industry which could benefit from such a coating is in footwear. Polyurethane-based soccer shoes suffer from degradation of the polymer caused by high humidity conditions and subsequent diffusion of water vapor across the membranes used in the shoe.

Integrated circuits suffer from problems of moisture and ion ingress which can result in failure of the circuit. Another problem is the diffusion of gold used in the gold/titanium ohmic contacts.

Magnetic media could also substantially benefit from such a coating. The degradation over time is often the result of high humidity conditions and physical wear of the material from contact with a read or write head.

Fiber optic conduits could also benefit because they suffer from the diffusion of gases and other fluids which causes their optical properties to degrade. Superconducting and photo diodes also suffer from diffusion barrier problems.

Fluid valves and solenoids also having sticking problems. Their moving parts tend to stick to their static components, resulting in intermittent or terminal component failure.

All of the problems described above can be alleviated to some degree, and even altogether eliminated in many cases by a coating which has the characteristics of being conductive, having a high degree of lubricity, providing bio-compatibility, flexibility, radio-opacity, diffusion resistance, wear and corrosion resistance, hardness, ability to be hydrophobic or hydrophilic, adherence to multiple materials, sterilizability, and chemical inertness and stability.

OBJECTS AND SUMMARY OF THE INVENTION

It is an object of the present invention to provide a conductive, non-stick coating which can be applied to materials which can benefit from exhibiting the property of having a surface which functions as if lubricated.

It is another object to provide a conductive, non-stick coating which has a non-stick coating which will not burn off, wear away or scrape away after repeated exposure to heat, friction and sharp edges.

It is another object to provide a conductive, non-stick coating which can flex with the material on which it is applied.

It is another object to provide a conductive, non-stick coating which is a ceramic.

It is another object to provide a conductive, non-stick coating which uses a conductive ceramic as the non-stick coating.

It is another object to provide a conductive, non-stick coating which is an amorphous ceramic coating that can flex without breaking or detaching itself from a substrate to which the coating is applied.

It is another object to provide a coating which can be applied to temperature-sensitive components which can also provide EMI and radio frequency interference (RFI) shielding.

It is another object to increase diffusion resistance for fluids and gases using the coating which is also flexible enough to prevent diffusion on flexing objects.

It is another object to provide a coating which can adhere to a plurality of different materials of an assembly so as to provide uniform protection.

It is another object to provide a coating which is chemically inert and stable so as to be usable in environments where it is important that the coating be nonreactive.

It is another object to provide a conductive, non-stick coating which uses transition metal nitrides, carbides and oxides as the ceramic coating.

It is another object to provide a conductive, non-stick coating which has the ceramic coating applied through sputtering to produce an amorphous ceramic coating.

It is another object to provide a conductive, non-stick coating which is cost effective to produce, and simple and efficient to apply to various substrate surfaces, including metals, plastics, composites, ceramics, semiconductors, magnets, and tissues.

It is another object to provide a conductive, non-stick coating which is radio-opaque, bio-compatible, diffusion resistant, corrosion resistant, sterilizable, and adherent in nature.

It is another object to provide a conductive, non-stick coating at or near room temperature, which permits the coating to be applied to many heat-sensitive materials and substrates such as plastics, semiconductors, magnets, and tissues.

In accordance with these and other objects of the present invention, the advantages of the invention will become more fully apparent from the description and claims which follow, or may be learned by the practice of the invention.

The present invention provides in a preferred embodiment a ceramic coating which is conductive, flexible and provides a surface which functions as if it were lubricated. The manufacturing process produces a coating of titanium nitride on a surface of a desired substrate material. The coating is amorphous, enabling the substrate to bend if desired.

One aspect of the invention is the considerably improved durability of the ceramic coating. Unlike other coatings, the present invention does not burn away, flake or scrape off after repeated exposure to heat and abrasion from sharp edges.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Figure 1:
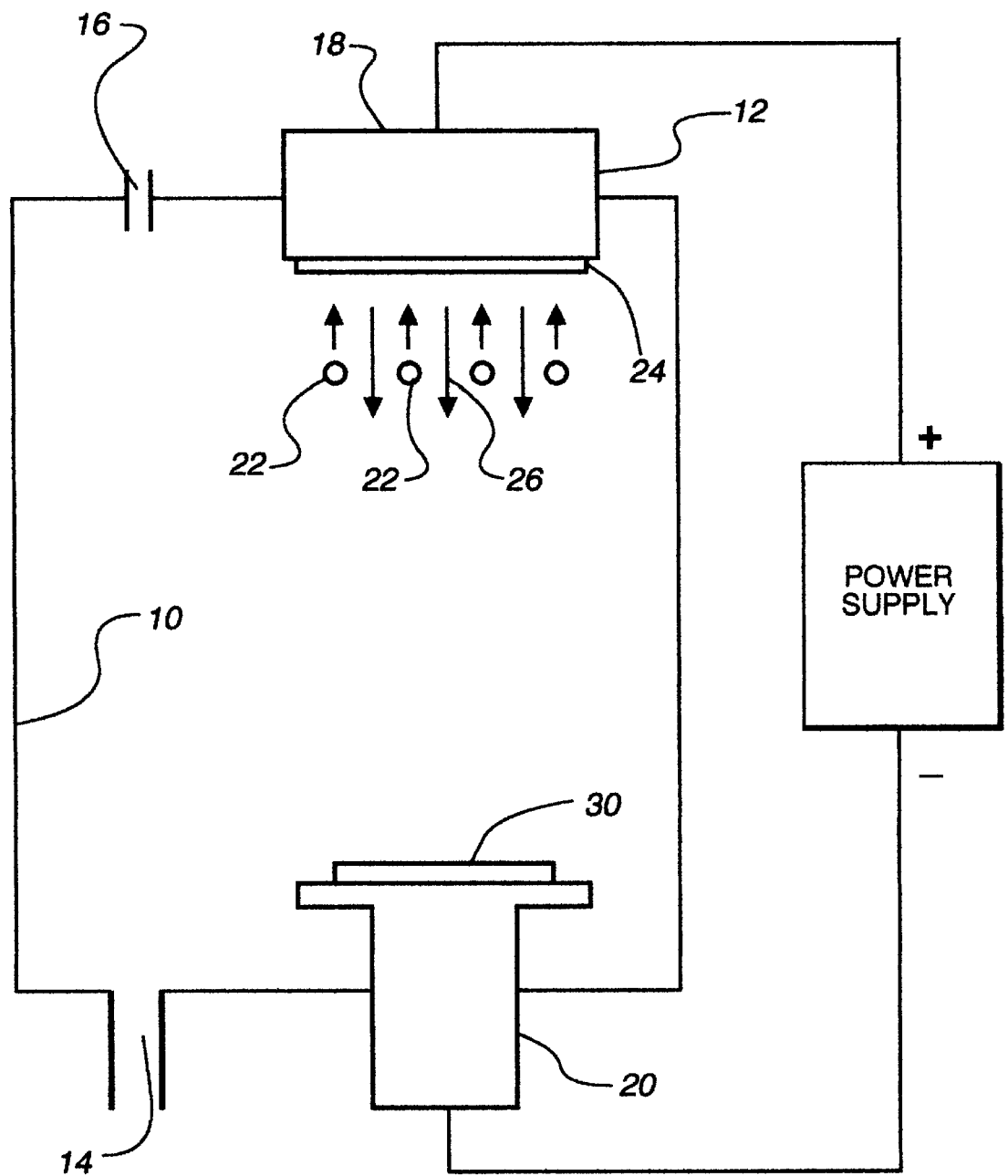
FIG. 1 is a schematic diagram of a sputtering chamber used in the direct sputtering manufacturing process of the present invention.

Reference will now be made to the drawings in which the various elements of the present invention will be given numerical designations and in which the invention will be discussed so as to enable one skilled in the art to make and use the invention. It is to be understood that the following description is only exemplary of the principles of the present invention, and should not be viewed as narrowing the claims which follow.

The present invention is comprised of a method of applying the conductive, non-stick coating, at or near room temperature, as well as the particular materials which can benefit from the coating in their normal use. In other words, devices, instruments and various apparatus can take advantage of being coated. These devices include those which can benefit from a conductive wear resistant coating which can also provide the benefits of being conductive and amorphous (and thus flexible).

Specifically, the conductive, non-stick coating is a ceramic coating. In the preferred embodiment, the ceramic coating is composed of titanium nitride (TiN) which is applied over the substrate by any appropriate method, such as those to be discussed later.

Advantageously, the ceramic coating of the present invention can be applied in relatively thin layers to substrates, typically on the order of Angstroms.

Most important to the present invention are the properties of the ceramic coating composed of TiN. It should also be mentioned that while the preferred embodiment uses TiN as the ceramic coating, there are other ceramics from the family of ceramics known as transition metal nitrides which might be used in the present invention. These ceramic coating materials include titanium nitride, among others. These materials are classified in terms of properties of hardness, corrosion resistance, color and high spectral reflectance (smoothness). What is important to the preferred embodiment of the present invention is that the material selected for the ceramic coating have the desirable characteristics of TiN. In electrosurgical instruments, it is appreciated that the most important of these characteristics are that the coating (a) be conductive, (b) act amorphous after application to the electrosurgical instrument, and (c) have a high degree of lubricity to thereby flow smoothly through tissue being cut/cauterized. It should also be realized that TiN can be used alone or in combination with other materials having desirable characteristics. These other materials might also include other conductive (transitional metal nitrides) or non-conductive ceramics.

Although never applied in an amorphous form by others using a room-temperature process in any of the applications to be described, Titanium Nitride is a ceramic whose crystalline form is well known for its advantageous properties of hardness, wear resistance, inertness, lubricity, biocompatibility, diffusion resistance, corrosion resistance and thermal stability in such applications where a low friction interface is needed to protect moving parts from wear. While it is the properties of electrical as well as thermal conductivity jointly with lubricity which make it attractive as a suitable coating for an electrosurgical blade, it is often the case that only one or two of the characteristics of the coating are used by the other embodiments of the present invention.

The preferred process of applying the coating to different substrates is the process of sputtering. However, it is helpful to know at this stage that advantageously, the TiN can be applied using sputtering at room or near-room temperatures, significantly simplifying the manufacturing process. TiN can also be applied with high dimensional accuracy to obtain an even coating thickness along all surfaces. As TiN can be applied at thicknesses in the Angstrom level, the coated part's dimensions are not materially affected. Furthermore, TiN exhibits a very high load carrying capacity and toughness. TiN also has excellent adhesion qualities so that it does not spall, even under plastic deformation of the surface. The high toughness and excellent adhesion properties are due to a metallurgical bonding between some substrates and the TiN coating. In particular, the TiN coating bonds well with other metals such as steel and stainless steel.

Most importantly, however, TiN advantageously has high hardness and low friction coefficients (referred to as lubricity). This property of lubricity enables the conductive, non-stick coating to glide through tissue for extended periods of time between cleaning. But unlike Teflon (™) coatings, TiN will not burn off or wear away quickly from repeated use to leave a substrate exposed. The ceramic TiN either has no wear, or wears substantially less than, for example, the Teflon (™) coating used in the prior art because Teflon (™) burns away, and peels off the substrate. Consequently, the present invention has a longer useful lifespan.

Most advantageously, the TiN ceramic coating of the present invention also has great flexibility. The coating process allows the TiN to be applied on surfaces which are not normally able to receive such a coating. This includes surface materials such as plastics, magnets, semiconductors, and other heat-sensitive materials including aluminum. The present invention also has a much stronger bond between a base metal substrate and its ceramic coating. This bond extends down to the molecular level. More specifically, there is a metallurgical bonding between a metallic substrate and the TiN coating. What is created is defined as an interfacial nanometer layer consisting of both the base metal substrate and the TiN ceramic coating. This interfacial zone is created in the first stage of the coating process when TiN is sputtered onto the base metal substrate. In other words, it is accurate to state that the TiN ceramic coating can be referred to as an amorphous bond, having no crystalline structure subject to fracturing. The amorphous TiN ceramic coating can therefore flex integrally with the base metal substrate to which it is attached.

When examining the potential applications of the non-stick coating of the present invention, the list is impressive, and ranges from simple devices to high-tech equipment. The following list is only provided as an example of applications. Items which can benefit from the ceramic coating of the present invention include scissors, knives, drill bits, reamers, saw blades, pliers, end mills, wire cutters, precision coining dies, rollers, pins, screws, bore gauges, stamp metal forming tools, extrusion dies, spool lips for spinning reels, counter bores, taps broaches, gear cutters, bearings bushings, gears, splines, actuators, push rods, cams, cam shafts, hobs, punches, valve stems, router bits, engine parts, blanking dies, resistance welding electrodes, scrapers, gouges, countersinks, counterbores, silicon wafers and chips, pump plungers, embroidery needles, VLSI semiconductors, compressor blades/vanes, jewelry, door hardware, writing instruments, eyeglass frames, shafts and seals, marine hardware, plumbing fixtures, slitters, aerospace components, plastic molds, dental instruments and devices, food processing equipment, key duplicators, forming dies, cutting tools, granulator blades, powdered metal dies, seaming rolls, burnishers, engravers, minting devices, razor blades, toy components, umbrellas, optical fibers, integrated circuits, video/audio heads, video/audio tapes, computer floppy disks, packaging, solar cells, kitchen utensils, window panes, golf clubs, bicycle components, reflectors, spark plugs, lamp shades, key chains, piston rings, fluid pumps, super conducting thin films, photo diodes, light emitting diodes, diode lasers, electrodes, electrochemical cells, thermolytic coolers, nuclear fuel pellets, magnetic recording media and heads, fluid valves, solenoids, disk drives, circuits to provide protection from EMI, circuit boards, belts, footwear, UV adhesives, tubing, casters, filters, paper products, actuators, fishing equipment, etc.

Some of the specific benefits which are provided by the ceramic coating include biocompatibility, a continuous coating, a smooth coating, a non-stick coating (reduces friction and eliminates galling and seizing), it is aesthetically appealing, corrosion resistant, wear resistant, fatigue resistant, sterilizable, generally radio opaque, applicable to flexible surfaces, adheres to a variety of surfaces which comprises different materials including composites, is applicable as a room-temperature process, does not introduce residual stresses, is conductive, is conformal and thin, and can act as a diffusion barrier.

Other applications include using the coating for integrated circuits. Specifically, integrated circuits currently use a titanium gold two-step process for the circuit. The coating should result in higher yield production, better purity, a higher diffusion barrier, equal or improved conductivity, applied in a one-step process instead of two, and should result in less expensive operation.

Regarding audio/video recording equipment and media, the potential benefits are increased head life and longevity of the media, improved quality of audio or video reproduction, less wear on the media, and the ability to coat plastics and thereby replace metal heads.

Regarding kitchen utensils such as pots and pans, the coating can be applied to aluminum, while Teflon (™) cannot, it will resist scratching and chipping better, it will result in a pot or pan with a longer life, it is nonstick, and metal spoons, spatulas and other metal utensils can be used without fear of damaging the coating.

Regarding plastic gears, the potential benefits are improved wear, less weight, lower costs, maintaining of dimensional accuracy, and longer life.

Regarding razor blades, there should be less skin irritation, lower costs of producing blades, improved quality, and a large marketing advantage.

Regarding spark plugs, the coating should provide longer life, reduced fouling and improved performance, particularly in the two cycle oil-mix variety.

In summary, the TiN ceramic coating of the present invention provides many unique advantages over the prior art. The TiN ceramic coating does not significantly wear or burn off, thereby providing improved reliability and durability, and not evolving by-product gases. Advantageously, the TiN ceramic coating can also be repeatedly cleaned so that the device which is coated can be reused many times. Furthermore, many different sterilization techniques can be used without damaging the TiN coating.

While the invention teaches that the substrate can be stainless steel, other materials can also be used. These other materials might also be conductive metals such as titanium, but can also include non-conductive materials such as plastics.

A final advantage in these non-medical applications described above concerns the manufacturing process for applying the ceramic coating. In a preferred embodiment, the TiN ceramic coating is applied to a stainless steel blade using a room temperature direct sputtering process. Sputtering is a room or relatively low temperature process by which a controlled thin film of Titanium Nitride is uniformly deposited on the stainless steel blade or any other substrate.

The sputtering process itself is relatively simple, and has numerous advantages for the present invention. For example, the sputtering process does not change the characteristics of the base metal substrate or the TiN ceramic coating. The other advantages become obvious with an examination of the sputtering process.

There are two forms of sputtering which are described herein. The first form of sputtering is known as direct sputtering. This means that the sputtering is done directly from a TiN source. TiN sources are available commercially, and pure TiN can be coated onto a base metal substrate using radio frequency sources in a non-reactive atmosphere.

Another method of applying TiN to a base metal substrate is through the process of reactive sputtering. In this process, the reactive atmosphere must be composed of nitrogen. The titanium reacts with the nitrogen atmosphere to form titanium nitride. The TiN then coats the surface of the stainless steel.

The process of both direct and reactive sputtering involves much of the same equipment as shown in FIG. 1. The sputtering takes place in a stainless steel chamber 10. In this preferred embodiment, the stainless steel chamber 10 has dimensions of approximately 18 inches in diameter and 12 inches in height. The actual sputtering function is accomplished by sputtering guns 12 which are generally located at the top of the stainless steel chamber 10. The sputtering guns 12 are capable of movement in both the horizontal and vertical directions as desired.

The sputtering system described above is accomplished using standard equipment readily available for manufacturing. An example of the direct sputtering process is as follows. The stainless steel chamber 10 is evacuated of ambient air through evacuation port 14. An inert gas such as argon is then fed into the stainless steel chamber 10 through a gas port 16. The argon gas is ionized using the cathode 18 and the anode 20 to generate an ion flux 22 which strikes the Titanium Nitride 24. The impact of the ion flux 22 will eject TiN sputtered flux 26 which travels and adheres to the base substrate 30. It is important to note that there are other sputtering processes well known to those skilled in the art which are also appropriate for applying the TiN ceramic coating 26.

While sputtering times may vary, experimentally it has been determined that the sputtering time is generally 1 to 1.5 hours to generate a TiN ceramic coating 26 on the base metal substrate 30 which is approximately 0.5 microns thick. Generally it has been found that the sputtering process applies the TiN sputtered flux 26 as a TiN ceramic coating 26 according to a linear function, so the application time is, easily adjusted accordingly to obtain the desired thickness. The 0.5 micrometer thick T4-N coating thus corresponds to a TiN deposition rate of approximately 1 angstrom thickness being added every second.

The process above has described the application process for applying the ceramic coating to a metallic substrate. In general, it is important to understand that sputtering is a momentum transfer process. It is a process wherein constituent atoms of the material are ejected from surface of a target because of momentum exchange associated with bombardment by energetic particles. The bombarding species are generally ions of heavy inert gas, usually argon. Sputtering may be used for both surface etching and/or coating. The flux of sputtered atoms that may collide repeatedly with the working gas atoms before reaching the substrate where they condense to form a coating of the target material.

A key difference between coating on metals and coating on plastics is that plasma is used to modify and/or pretreat the surface of the plastic to a greater extent on plastics than on metals. For coating certain plastics such as silicone, a plasma treatment can be given in a separate chamber or by using the same sputtering machine used for coating at lower energy levels at which plasma forms but no or minimal sputtering occurs. This pre-treatment helps the coating adhere better to the plastic substrate. For the pre-treatment of plastics to be coated, the plastic surface is in contact with the plasma, and plasma ion bombardment on the surface modifies the plastic surface by plasma etching which is more conducive to receiving the target atoms. This promotes a dense, fine-grained amorphous structure on the surface depending on the process conditions such as pressure and power. The bombardment effects will give the target atoms enough energy to get into the surface layers of the plastic, thereby giving excellent bonding of the coating with the substrate. The flux of sputtered material leaving the target will be identical in composition to the target.

The quality of the coating depends on the sputter emission directions, the gas phase transport, and the substrate-sticking coefficient of the constituents. Because the coating target material transfers to vapor phase by a mechanical process (momentum transfer) rather than by a chemical or thermal process, the heating of the substrate can be controlled by carefully adjusting the conditions (keeping sputtering energy levels and thus temperatures low). This adjustment makes it possible to coat plastic surfaces at room or near room temperature without damaging the substrate.

While the presently preferred method of application of the ceramic to the substrate is through sputtering, it should be apparent that there are other methods. These include such methods as CVD and plasma deposition. Therefore, the application method of sputtering should not be considered limiting in the present invention.

It should be mentioned that TiN also differs from other state of the art coatings for base metals in that it does not evolve dangerous gases. When heated, TiN does not evolve any gases.

While the presently preferred embodiment of the invention emphasize the amorphous coating of a ceramic on the base metal substrate, it should also be realized that crystalline coatings can also be used.

The materials to which the ceramic coating of the present invention is applied above are generally considered those which are found specifically in non-medical applications. However, the obvious benefits of the present invention to the medical industry should be examined carefully because of the substantial benefits that can result.

From a short list of the medical devices, implants and instruments which can be coated with the ceramic coating of the present invention, the advantages of the present invention become more obvious. First, mechanical devices which can benefit from the present invention include blood pumps such as Ventricular Assist Devices, Artificial Hearts, Intra-Aortic Balloon Pumps and Impellers. The coating is applied to most plastic, metallic and ceramic components including magnets which can be coated at the room or near room temperature process to thereby not affect the magnetic properties. Furthermore, the coating provides such advantageous features as bio-compatibility including non-toxicity, even when the underlying material might not be bio-compatible. The coating can also function as corrosion resistance, and even as a diffusion barrier.

Not only can the coating of the present invention be applied to the blood-contacting surfaces, but also to the exterior of implanted device. Such devices include balloons such as epitaxis, catheter, occluder, intra-aortic balloons and angioplasty balloons. The coating can also be disposed on diaphragms, volume displacement chambers, and associated fluid paths in plastic tubes.

When addressing motors, the coating can also be used on bearings and bearing components. These components include balls, pivots, and inner and outer races used in actuators for medical devices. The result is a reduction in wear and thus increased lifespan of the medical devices.

Other medical devices that can benefit are catheters, especially those used in long-term indwelling procedures, cardiotomy and cerebrovascular, and those needing a safer and more reliable radio-opaque covering or marker. Soft-tissue implants include intravaginal and colostomy pouches, breast implants, penile and testicular implants.

Valves of the type used in hearts can also be improved by the coating disposed on disks and struts. Existing stents made from metal, ceramic and plastic and used for an annulplasty ring can be coated to provide the desired flexible and bio-compatible outer covering.

Shunts such as a dialysis shunt, an A-V shunt, a central nervous system shunt, an endolymphatic shunt tube, a peritoneal shunt and a hydrocephalys shunt can also be coated.

Silicone-based medical devices including inhaler seals, valves for laryngechtomy prostheses, nasal tampons, and tubes can also be coated.

The present invention can also serve to coat a plastic sheath covering current-carrying loads, as well as the leads themselves, connectors, feedthroughs for any implanted, electrically powered device such as a pacemaker, defibrillator, cardioverter, bipotential electrodes and leads, neural stimulators such as a cerebellar, brain, cranial, nerve and spinal cord device. The implanted devices can also be optical or cochlear in nature.

Other devices that can benefit include arterial filters, vascular grafts, varicose vein cuffs, as well as intracardiac, pledget, pericardial and epicardial patches. Contraceptive and Ob/Gyn devices include a plug prostheses, tubal occlusion devices (band, clip, insert and valve), urethral devices such as a stent, dilator and a catheter, IUDs and diaphragm. Other devices include an angiographic and other guide wire.

Sensors and transducers which are of the implantable variety as well as the non-implantable short-term variety can be coated. These include those used in measuring blood flow, blood pressure, vascular access devices, those which can be protected with a conductive layer of the coating, a catheter tip pressure transducer, and an invasive glucose sensor. The coating itself can be used as sensing material which detects changes in its property such as conductivity as a function of the thing being measured.

Occluders include those used in patent ductus arteriosus. A tracheotomy tube can also be coated.

Finally, hermetically sealed cans and other enclosures having a plastic-based substrate can be coated, including those used to encase electronics of any type, for actuators, sensors and fluids.

Surgical instruments and devices can also be coated. Such devices include catheters of all types, needles, trocars, feeding/breathing tubes, transfusion tubes, clips, surgical staples, electrosurgical instruments, pumps, as well as knives, scalpels, scissors, clamps, coagulators, is dilators, retractors, examination gloves, non-absorbable sutures and ligatures, microtomes, surgical meshes, tonsil dissectors, and vascular clamps, stereotaxis instruments and accessories, and heat exchangers.

There are also various orthopedic devices that can be coated, such as synthetic ligaments and tendons, fallopian tube replacements, ear prostheses, Stiennman Pins, bone plates and skull plates.

Measuring and analytical devices include blood measuring and evaluating devices, blood collection systems, containers for blood and other sensitive fluids, linings, tubes and blood-contacting surfaces of laboratory instruments, and coatings for leads used in such things as an EEG, ECG, etc.

Other devices that can be coated are syringes, plungers, intra ocular lenses, drug containers and packaging.

It should ne be surprising that the preceding pages do not represent an exhaustive list of all of the possible medical devices, instruments and applications of the present invention, but it serves to suggest many of the applications.

One particularly important medical application of the present invention is in diffusion barriers. Many implantable devices such as a blood pump, as well as soft-tissue implants (breast, penile and testicular) have diffusion barriers containing fluids. The diffusion barriers are supposed to prevent the passage of working fluids (such as a lubricating oil) from within the medical device to the body. Likewise, body fluids (blood) are not supposed to enter into the medical device. However, it is the case that diffusion barriers are soft membranes which are disadvantageously permeable to gases and fluids. The present invention functions as a diffusion barrier to prevent or at least reduce the passage of gases and fluids through the permeable membranes.

Figure 2:
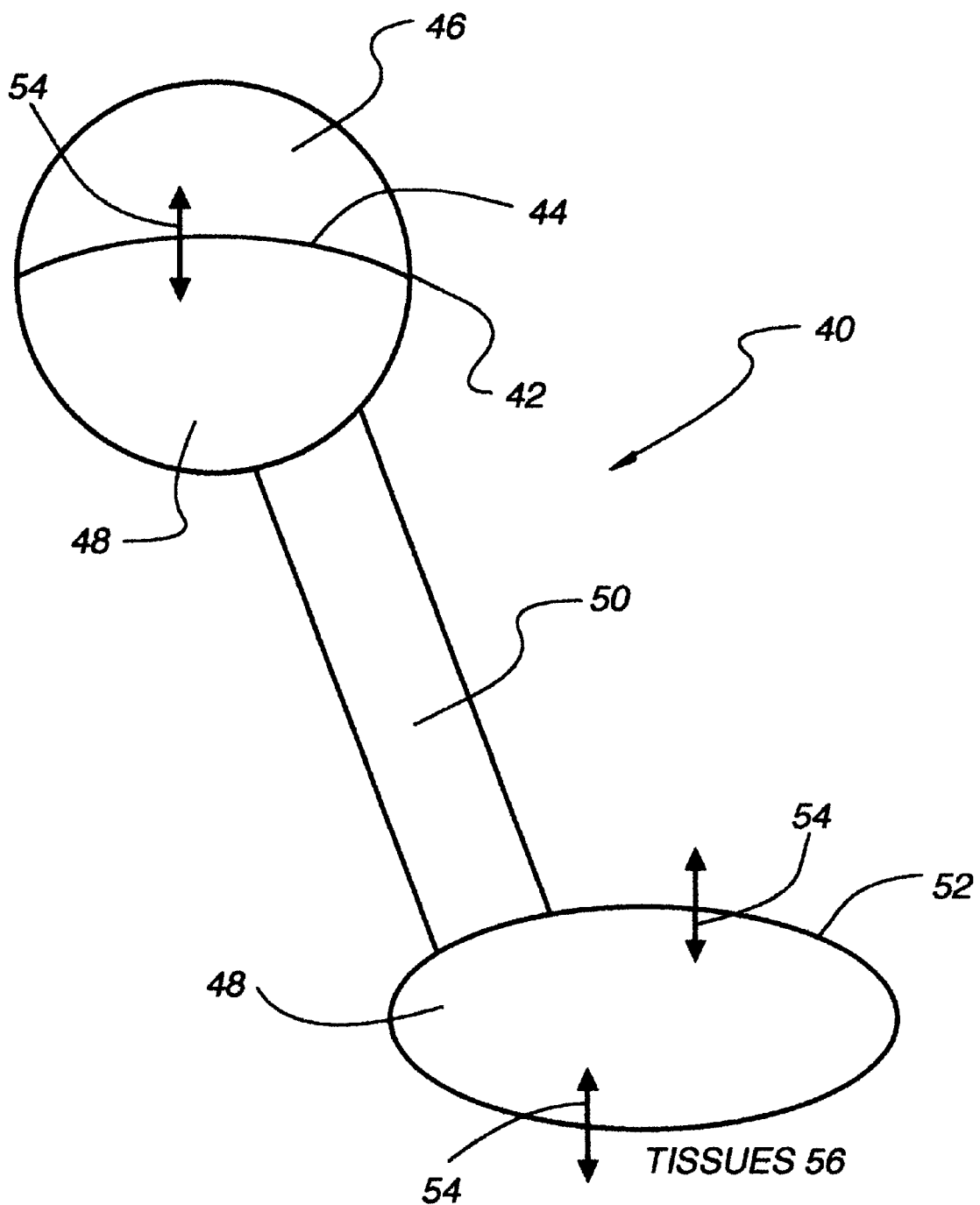
FIG. 2 is a diagram of the components of a pulsatile blood pump, showing where diffusion of gases and liquids occurs which leads to failure or reduced performance of the pump, and possible health consequences to the patient.

To understand the nature of the problem, it is helpful to look at a diagram of a pulsatile blood pump. FIG. 2 is a blood pump 40. The blood pump 40 has a pumping chamber 42 in which is disposed a polyurethane membrane 44 which functions as a diaphragm. On one side of the membrane 44 is blood 46. On the other side of the membrane 44 is a working fluid 48 of the blood pump 40. The pumping chamber 42 is coupled via an energy converter 50 to a volume displacement chamber 52. Within the volume displacement chamber 52 is the working fluid 48 of the blood pump 40.

The arrows 54 indicate that diffusion occurs through the membrane 44 between the blood 46 and the working fluid 48 in the pumping chamber 42, and between the working fluid 48 and tissues 56 which surround the volume displacement chamber 52. It should be remembered that the working fluid 48 of the blood pump 40 is typically some of type of lubricating oil such as silicone oil. Obviously, it is desirable to prevent blood 46 and working fluid 48 from passing through the flexible membrane 44.

Presently, existing pulsatile pumps accept diffusion of blood and working fluids, and simply try to treat the symptoms of the problem. In other words, the pulsatile pumps are often provided with a priming port for receiving gas or working fluids.

Allowing diffusion is detrimental to the pulsatile pumps for several reasons. First, providing a priming port enables contaminants to enter into the device, thus increasing the chances of infection. Second, the passage of blood into the pumping mechanism increases speed of corrosion of internal components, and thus increases the chances of failure of the device.

There remain unanswered questions regarding the long-term health effects of silicone. It is reported that connective tissue diseases and breast cancer are one result. However, it is obviously prudent to reduce the introduction of silicone oils into the blood stream.

It has been determined experimentally that some pulsatile blood pump devices will lose between 10 and 15 cc's of silicone oil into the body per year. The loss of this volume of working fluid is also detrimental to the operation of the device because it reduces the stroke volume, for example, by 15% to 25%. Such a loss in stroke volume is likely to be an unacceptably high loss. However, electrohydraulic pumps are not the only ones whose performance suffers from diffusion. Pusher-plate devices are also susceptible to failure.

Referring to the volume displacement chambers, the membranes used in these chambers also allow body fluids into the device. These body fluids contain ions and moisture which cause corrosion and wear of the blood pump's energy converter, thus leading to eventual failure of the pump due to short-circuiting or corrosion.

Previous attempts to reduce permeability of the membrane have failed to stop diffusion. For example, multiple membrane layers or different membrane materials have been tried. Unfortunately, none of these attempts have succeeded.

The present invention advantageously reduces diffusion of working fluids and blood through the membrane by coating the membrane with a flexible, bio-compatible, corrosion resistant ceramic coating.

Figure 3:
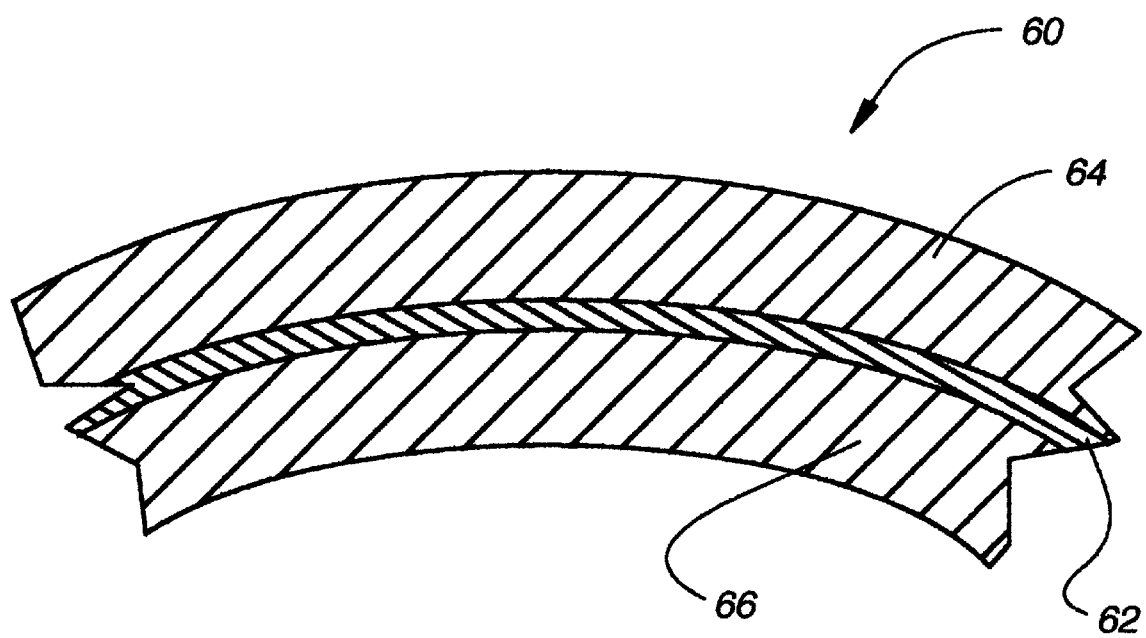
FIG. 3 is a cross-sectional diagram of the presently preferred embodiment for a diffusion barrier in medical devices.

FIG. 3 is a cross-sectional profile view of the presently preferred embodiment of a membrane 60 to be used in a pumping mechanism. In the presently preferred embodiment, a layer of the ceramic coating 62 is disposed between two layers 64 and 66 of the membranes. In this embodiment, polyurethane is used for the membranes 64 and 66.

The thickness of the ceramic coating 62 has experimentally been determined to be within the range of approximately 5000 to 10,000 angstroms. The ceramic coating 62 is deposited on one of the polyurethane membranes 64 or 66 after vacuum forming or solution casting. During sputtering, the polyurethane surface is energized by the argon plasma. Accordingly, the ions of the ceramic coating material will actively bond with the surface, thus creating a diffusion layer which is amorphous.

The second layer of polyurethane will form an active surface while heated during vacuum forming. During solution casting, the polymer will be in a liquid phase, enabling the polyurethane to enter surface micro-irregularities of the ceramic coating. This bonding will prevent surface delamination.

Because amorphous Titanium Nitride is inert, fatigue resistance, biocompatible, corrosion resistant and lightweight. Furthermore, TiN is hydrophobic, and thus prevents the diffusion of any liquids through its surface. It is possible to also make the surface hydrophilic by appropriate surface plasma treatments. Diffusion occurs predominantly along grain boundaries. Since the amorphous nature of the TiN coating does not have any grain boundaries, diffusion through the TiN ceramic layer 62 is greatly reduced.

When examining other materials to use as a diffusion barrier coating between the polyurethane layers, it is observed that gold can also be sputtered. However, gold is likely to fail due to its low fatigue resistance under continuous flexing and stretching conditions of the membrane in a blood pump. Furthermore, gold is relatively expensive compared to TiN. Silver and copper are corrosive and hence cannot be used in this medical application.

However, it is possible that other ceramics of the family of TiN can be used as the diffusion barrier. These ceramics include Aluminum Oxide, Titanium Carbide, Silicon Carbide, Silicon Nitride, Boron Nitride and Zirconia. The advantages of these ceramics is that like TiN, they provide an amorphous coating through sputtering, they also inhibit permeability of gases and fluids, they can be deposited at room or near-room temperature, they can be applied to multiple materials to thereby provide a same coating on different parts and materials of the pump, and they are all bio-compatible.

It is to be understood that the above-described embodiments are only illustrative of the application of the principles of the present invention. Numerous modifications and alternative arrangements may be devised by those skilled in the art without departing from the spirit and scope of the present invention.

What is claimed is:

1. A method for providing a wear-resistant ceramic coating on a substrate which is used in an abrasive environment, such that the substrate is not deformed during a process of applying the wear-resistant ceramic coating to the substrate, said method comprising the steps of:

selecting at least one ceramic from a group of ceramics consisting of transition metal nitrides;

using a generally room temperature application process to apply said at least one selected ceramic as an angstrom-thick, continuous, conductive and amorphous ceramic coating directly on the substrate in the absence of a sub-coating;

said amorphous ceramic coating bonding to the substrate by way of an interfacial nanometer-thick bonding layer that consists of both the substrate and said at least one selected ceramic;

the substrate not being damaged by said generally room temperature application process;

said amorphous ceramic coating being characterized as not having a crystalline structure;

said amorphous coating having no grain boundaries; and said amorphous coating having uniform properties and deformation behavior at the nanometer level, thereby enabling the substrate and said amorphous ceramic coating to be deformed without fracturing.

2. The method defined in claim 1 wherein the method further comprises the step of applying at least one material which is not a transition metal nitride to said amorphous ceramic coating.

3. The method defined in claim 1 wherein said amorphous ceramic coating is electrically conductive to thereby facilitate propagation of electrical energy within said amorphous ceramic coating.

4. The method defined in claim 1 wherein said amorphous ceramic coating is not worn away by application of RF energy thereto, by abrasion or by sterilization.

5. The method defined in claim 1 wherein the method further comprises the step of physically deforming the substrate from a resting state, and wherein said amorphous ceramic coating deforms as the substrate is deformed, without damage to said amorphous ceramic coating.

6. The method defined in claim 1 wherein said amorphous ceramic coating is a corrosion resistant amorphous ceramic coating.

7. The method defined in claim 1 wherein said amorphous ceramic coating is a fatigue resistant amorphous ceramic coating.

8. The method defined in claim 1 wherein said amorphous ceramic coating is sterilizable and biocompatible.

9. The method defined in claim 1 wherein said amorphous ceramic coating is radio frequency opaque.

10. The method defined in claim 1 wherein said amorphous ceramic coating is a generally smooth and non-stick amorphous ceramic coating.

11. The method defined in claim 1 wherein said at least one selected ceramic is titanium nitride.

12. The method defined in claim 1 wherein the substrate is selected from a group consisting of plastic, glass, ceramic, metal, composites, magnetic material and semiconductor.

13. The method defined in claim 1 wherein said amorphous ceramic coating forms a shield against electro magnetic interference.

14. The method defined in claim 1 wherein said amorphous ceramic coating is a chemically inert and chemically stable amorphous ceramic coating.

15. The method defined in claim 1 wherein said amorphous ceramic coating forms a diffusion barrier that inhibits fluids and gases passing through said amorphous ceramic coating.

16. The method defined in claim 15 wherein the substrate member and said amorphous ceramic coating are flexible to thereby enable flexing of the substrate without damaging said diffusion barrier.

17. The method defined in claim 16 wherein said diffusion barrier operates to inhibit exchange of gases or fluids through said diffusion barrier.

18. The method defined in claim 17 wherein the substrate is a flexible membrane that is permeable by fluids and gases.

19. The method defined in claim 1 including the steps of:
providing a single assembly having a plurality of different substrate members; and
applying said amorphous ceramic coating to said plurality of different substrate members such that said amorphous ceramic coating is applied to all surfaces of said single assembly.

20. The method defined in claim 1 wherein the substrate is selected from a group of magnetic members consisting of magnetic tape, ceramic magnets, rare-earth magnets, metallic magnets, and wherein said selected magnetic member is protected from moisture by said amorphous ceramic coating.

21. The method defined in claim 1 wherein the substrate is rotatable magnetic media, and wherein said amorphous ceramic coating reduces a surface friction of said rotatable magnetic media.

22. The method defined in claim 1 wherein said amorphous ceramic coating provides protection from EMI and RFI.

23. A method for providing a ceramic coating on a semiconductor material, said method comprising the steps of:
selecting a ceramic from a group of ceramics consisting of transition metal nitrides;
using a generally room temperature application process to apply said selected ceramic as a thin amorphous ceramic coating directly onto the semiconductor material in the absence of a sub-coating;
said amorphous ceramic coating bonding to the semiconductor material by way of an interfacial nanometer thick bonding layer that consists of both the semiconductor material and said selected ceramic; and
said amorphous ceramic coating forming a continuous, conductive, and amorphous coating which is not characterized as having a crystalline structure, to thereby enable said amorphous ceramic coating to be deformed without fracturing.

24. A method for providing a wear-resistant ceramic coating on a magnetic member whose magnetic properties can be damaged by thermal energy, such that the magnetic member retains its magnetic properties during a process of applying the wear-resistant ceramic coating to the magnetic member, said method comprising the steps of:
selecting a ceramic from a group of ceramics consisting of transition metal nitrides;
using a generally room temperature application process to apply said selected ceramic directly to the magnetic member in the absence of a sub-coating and as a thin and continuous amorphous coating;
said amorphous coating bonding to the magnetic member by way of an interfacial nanometer-thick bonding layer that consists of both the magnetic member and said selected ceramic;
the properties of the magnetic material not being damaged by thermal energy of said generally room temperature application process; and
said amorphous coating being a coating that does not have a crystalline structure, to thereby enable said amorphous coating to deform without fracturing.

25. A method for providing a wear-resistant ceramic coating on a heat-sensitive member which is used in an abrasive environment, such that the heat-sensitive member is not damaged or degraded during a process of applying the wear-resistant ceramic coating onto the heat-sensitive member, said method comprising the steps of:
selecting a ceramic from a group of ceramics consisting of transition metal nitrides;
using a generally room temperature application process to apply said selected ceramic as an angstroms-thick, wear-resistant, ceramic coating directly on the heat-sensitive member in the absence of a sub-coating;
said wear-resistant ceramic coating bonding to the heat-sensitive member by way of an interfacial thick-thick bonding layer that consists of both the heat-sensitive member and said selected ceramic;
the heat-sensitive material not being deformed by heat generated by said generally room temperature application process;
said wear-resistant ceramic coating forming a continuous, conductive, and amorphous coating on the heat-sensitive member; and
said wear-resistant ceramic coating not having a crystalline structure, to thereby enable said wear-resistant ceramic coating to be deformed without fracturing said wear-resistant ceramic coating.

26. A method for providing a wear-resistant ceramic coating on a material that is usable in an environment that is detrimental to the material, such that the material is covered with a continuous, smooth and fatigue-resistant ceramic coating, said method comprising the steps of:
selecting a ceramic from a group of ceramics consisting of transition metal nitrides;
using a generally room temperature application process to apply said selected ceramic as an angstroms-thick, wear-resistant, ceramic coating directly on the material in the absence of a sub-coating;
said wear-resistant ceramic coating bonding to the material by way of an interfacial nanometer-thick bonding layer that consists of both the material and said selected ceramic;
said wear-resistant ceramic coating enhancing wear-resistance, lubricity and strength of the material; and
said wear-resistant ceramic coating being a continuous, conductive, and amorphous ceramic coating that cannot be characterized as having a crystalline structure, to thereby enable the wear-resistant coating to be deformed without fracturing.

27. The method defined in claim 26 wherein the material is selected from a group of products consisting of kitchen utensils, gears, spark plugs, molds, plumbing fixtures, eyeglass frames, cutting instruments, moisture barriers, sporting goods, writing instruments, drilling instruments, fasteners, bearings, bushings, electrical devices, semiconductors, jewelry, engine components, toys, packaging, optical instruments, fuel cells, and recording media.

28. A method for providing a wear-resistant ceramic coating on a ceramic member which can be damaged by thermal energy, such that the ceramic member is not damaged during a process of applying the wear-resistant ceramic coating to the ceramic member, said method comprising the steps of:

provdiing a quantity of titanium nitride ceramic;

using a generally room temperature application process to apply said titanium nitride ceramic as an angstrom-thick, wear-resistant, ceramic coating directly to the ceramic member in the absence of a sub-coating, and such that the ceramic member is not damaged by said generally room temperature application process;

said wear-resistant ceramic coating bonding to the ceramic member by way of an interfacial nanometer-thick bonding layer that consists of both the ceramic member and said titanium nitride ceramic;

said wear-resistant ceramic coating forming a continuous, conductive, and amorphous ceramic coating on the ceramic member that does not have a crystalline structure, to thereby enable said wear resistant coating to be deformable without fracturing.

29. A method providing a bio-compatible coating on a temperature-sensitive member used in a medical device such that the temperature sensitive member is not damaged during a process that applies the bio-compatible coating to the temperature sensitive member, said method comprising the steps of:

selecting a ceramic from a group of ceramics consisting of transition metal nitrides;

using a generally room temperature application process to apply said selected ceramic as a thin bio-compatible ceramic coating directly on the temperature-sensitive member in the absence of a sub-coating, such that the temperature-sensitive member is not damaged by thermal energy of said generally room temperature application process;

said bio-compatible ceramic coating bonding to the temperature-sensitive member by way of a nanometer-thick interfacial layer that consists of both said selected ceramic and the temperature-sensitive member;

said bio-compatible ceramic coating forming a continuous, conductive, and amorphous coating not having a crystalline structure, to thereby enable the bio-compatible ceramic coating to be deformable without fracturing; and placing the temperature-sensitive member and its bio-compatible ceramic coating in the medical device, to thereby enable the medical device to be utilized in a medical environment.

30. The method defined in claim 29 wherein the temperature sensitive member is selected from a group consisting of plastic, glass, and magnetic materials.

31. The method defined in claim 30 wherein said selected ceramic provides corrosion resistance.

32. The method defined in claim 30 wherein said selected ceramic provides lubricity.

33. The method defined in claim 29 wherein the temperature-sensitive member is a plastic introducer catheter which is easily inserted due to said lubricity.

34. The method defined in claim 29 wherein the temperature-sensitive member is at least one permanent magnet used in an implantable medical device that requires at least one electromagnetic device for operation of the implantable medical device.

35. A method for utilizing a nonbio-compatible member in an implantable medical device, wherein the implantable medical device is made safe for implantation, said method comprising the steps of:

selecting a bio-compatible ceramic from a group of ceramics consisting of transition metal nitrides;

using a generally room temperature application process to apply said selected bio-compatible ceramic as an amorphous coating directly onto the nonbio-compatible member in the absence of a sub-coating;

said amorphous coating having a thickness in the range of from about 5,000 to about 10,000 angstroms;

said amorphous coating bonding to the nonbio-compatible member by way of an nanometer-thick interfacial layer that consists of both said selected bio-compatible ceramic and the nonbio-compatible member;

said amorphous coating forming a continuous, conductive, and amorphous coating that completely covers the nonbio-compatible member;

said amorphous coating having substantially no crystalline structure, to thereby enable said amorphous coating to be deformable without fracturing; and placing the coated nonbio-compatible member in the implantable medical device.

36. The method defined in claim 35 wherein the nonbio-compatible member is selected from a group of temperature-sensitive members consisting of plastic, glass, and magnetic members.

37. The method defined in claim 35 wherein the implantable device is selected from a group consisting of stents, ventricular assist devices, pumps, impellers, balloons, diaphragms, volume displacement chambers, plastic tubes providing fluid paths, bearings, bearing components, catheters, occluders, soft tissue implants, valves, shunts, pacemakers, defibrillators, cardioverters, electrodes, neural stimulators, filters, grafts, patches, contraceptive devices, sensors, transducers, needles, medical tubes, clips, surgical staples, prostheses and electrosurgical blades.

38. A method for creating a diffusion barrier within a medical device, the diffusion barrier being disposed on a permeable membrane through which fluids and gases will normally diffuse, said method comprising the steps of:

selecting a ceramic from a group consisting of titanium nitride, aluminum oxide, titanium carbide, silicon carbide, silicon nitride, born nitride and zirconia;

using a generally room temperature process to apply said selected ceramic directly onto the permeable membrane as a diffusion barrier in the absence of a sub-coating;

said diffusion barrier being from about 5,000 to about 10,000 angstroms thick;

said diffusion barrier bonding to the permeable membrane by way of a nanometer-thick interfacial layer that consists of both said selected ceramic and the permeable membrane;

said diffusion barrier forming a continuous amorphous coating on the permeable membrane;

said diffusion barrier having no appreciable crystalline structure; and said diffusion barrier reducing penetration of fluids and gases through the permeable membrane.

39. The method defined in claim 38 wherein the permeable membrane operates to reduce an exchange of working fluids that are within the medical device and body fluids that are within a body in which the medical device is implanted.

* * * * *